United States Patent [19]
Fitzky et al.

[11] 4,206,399
[45] Jun. 3, 1980

[54] APPARATUS FOR DETERMINING THE WATER CONTENT OF ISOTROPIC MATERIALS BY MEANS OF MICROWAVE ABSORPTION

[75] Inventors: Hans G. Fitzky, Odenthal; Franz Schmitt, Cologne; Norbert Bollongino; Helmut Rehrmann, both of Leverkusen, all of Fed. Rep. of Germany

[73] Assignee: Bayer Aktiengesellschaft, Leverkusen, Fed. Rep. of Germany

[21] Appl. No.: 890,764

[22] Filed: Mar. 27, 1978

[30] Foreign Application Priority Data

Apr. 9, 1977 [DE] Fed. Rep. of Germany ....... 2715947

[51] Int. Cl.[2] .............................................. G01R 27/04

[52] U.S. Cl. ............................ 324/58.5 C; 324/58.5 B

[58] Field of Search ...................... 324/58.5 B, 58.5 A, 324/58.5 C, 58 B, 58 C, 58 R

[56] References Cited

U.S. PATENT DOCUMENTS

| | | | |
|---|---|---|---|
| 2,548,598 | 4/1951 | Feiker, Jr. | 324/58.5 C |
| 2,611,804 | 9/1952 | Zaleski | 324/58.5 B |
| 2,671,884 | 3/1954 | Zaleski | 324/58.5 C |
| 3,348,140 | 10/1967 | Godding | 324/58.5 A |
| 3,379,971 | 4/1968 | Albanese | 324/58.5 B |

FOREIGN PATENT DOCUMENTS

| | | | |
|---|---|---|---|
| 45-20237 | 7/1970 | Japan | 324/58.5 C |
| 1251362 | 10/1971 | United Kingdom | 324/58.5 B |
| 1334791 | 10/1973 | United Kingdom | 324/58.5 C |
| 240775 | 8/1969 | U.S.S.R. | 324/58.5 C |

*Primary Examiner*—M. Tokar
*Attorney, Agent, or Firm*—Sprung, Felfe, Horn, Lynch & Kramer

[57] ABSTRACT

The principle of measurement is based on the microwave absorption by the water content of a sample. The sample is located in a closed single-reflection measurement cell which is fed by a microwave oscillator which is frequency-modulated within the absorbing frequency range of the sample. The sample partially or completely fills the end section of a circular or rectangular waveguide forming the measurement cell. The waveguide is sealed off with a short circuit plate so that two planar travelling waves with a homogeneous field distribution are present in the measurement cell.

20 Claims, 7 Drawing Figures

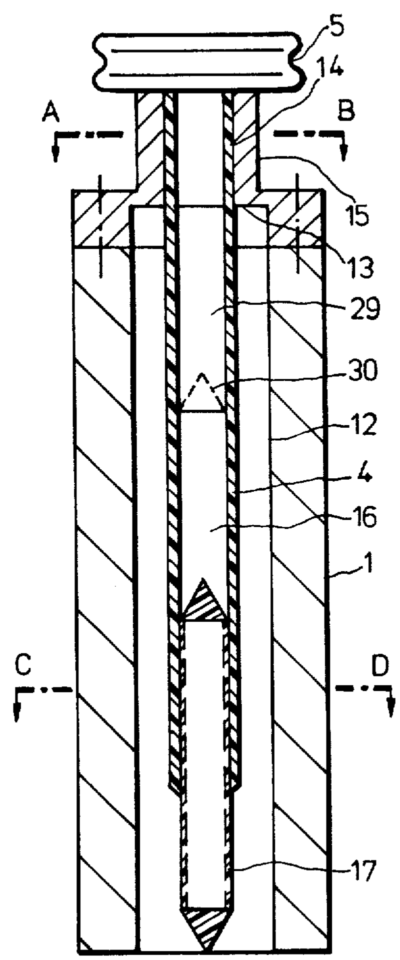
FIG. 3
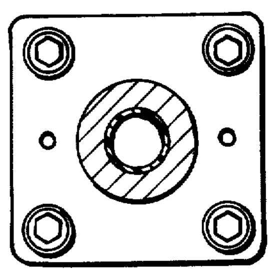
FIG. 4 (A-B)
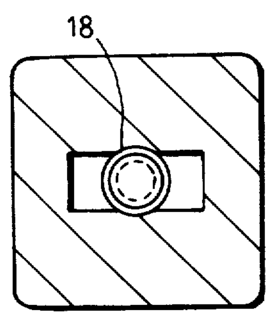
FIG. 5 (C-D)

APPARATUS FOR DETERMINING THE WATER CONTENT OF ISOTROPIC MATERIALS BY MEANS OF MICROWAVE ABSORPTION

The invention relates to an apparatus for measuring the water content of electrically non-conductive powders, granulates, pastes and other isotropic materials.

The apparatus consists basically of a microwave oscillator which feeds a closed single reflection measuring cell, charged with the sample, in a transmission arrangement.

It is very important to be able to determine rapidly the water content of powders, granulates, pastes and fibrous materials for large-scale production of these materials. Examples of such materials include pharmaceutical products, plastics granulates, raw materials for washing agents and finished products, building materials and ceramic pre-products and agricultural produce.

In order to monitor the industrial production and processing of these products, it is necessary to use a rapid action measuring instrument the measurements from which may be used to control operation or to control quality during final inspection.

Apparatuses described in the literature for measuring the water content of bulk products, pastes and other materials are usually designed as free jet apparatuses which are provided for monitoring continuously moving material and which only give relatively inaccurate results owing to the varying bulk density and reflection of the measuring beam, or whose technical design is not suitable for rapid and precise routine measurement in operational laboratories (German Offenlegungsschrift No. 2,017,061 and German Offenlegungsschrift No. 2,309,278). Microwave moisture-measuring apparatus for powdery or granular products are described in the "GIT Fachzeitschrift für des Laboratorium", 1974 Volume, pages 869 to 880 and pages 994 to 1000. The change in quality of a resonator owing to the sample is used as the unknown. The resonator is fed by a frequency-modulated microwave oscillator. The frequency deviation is selected sufficiently large for the resonance curve of the resonator to be completely covered both when it is empty and when it is full of sample. Downstream of the transmission resonator is located a microwave detector emitting a direct voltage signal which is a direct measure of the moisture content of the material. However, when operating with such apparatus, the accuracy of measurement has been found to vary widely. It has been found that the accuracy depends upon the quantity of sample. Furthermore, even slight variations in the bulk density of the product have been found to influence the measurements considerably. The last-mentioned effect interferes particularly when such apparatus are used in the laboratory as routine measurement apparatus.

The apparatus described above was originally designed for examining small quantities of material having moisture content within the range considered as being residual moisture (for example from 0.1 to 5 g of substance and from 0.01 to 0.5% by weight of $H_2O$). However, when dealing with small to average volumes of sample between about 1 and 1000 $m^3$ having a moisture content of between about 0.5 and 25% by weight, a closed single reflection measurement cell is preferable to a resonator. In addition, the considerable frequency detuning and change in adaptation must be taken into consideration.

The object of the invention is therefore to provide a measuring apparatus for measuring moisture in the range of from 0.5 to 25% by weight of isotropic materials, for example powdery products, based on a microwave transmission arrangement with a single reflection measurement cell. As high accuracy as possible is to be obtained even with different quantities of sample without slight variations in the bulk density influencing the measured result to a significant degree.

According to the invention there is provided an apparatus for measuring the water content of an electrically non-conductive isotropic material, comprising a microwave oscillator, frequency-modulated within the absorbing frequency range of the material, a closed, single-reflection, measurement cell, adapted to be charged with a sample of the material in a container, and supplied with microwaves from the oscillator, the measurement cell being in the form of a waveguide of circular or rectangular cross-section terminated by a short-circuit plate, so that two planar travelling waves with a homogeneous field distribution are present in the measurement cell, and an instrument for measuring the microwave signal transmitted through the sample, the container partially or completely filling at least an end section of the measurement cell.

The super-position of a wave running forwards and a wave running backwards produces undesirable inhomogeneity of the measured (electric field strength) depending on location, which may be eliminated by suitable choice of the modulation frequency. The time average of the measured field may be rendered practically completely uniform by using a frequency deviation causing the field maxima to be displaced by a quarter of a wavelength.

The homogenisation may be further improved by filling the tubular conductor upstream of the short-circuit plane with a loss-free dielectric of length $l=n\lambda/2\sqrt{\epsilon'}$ where $\epsilon'$ is the dielectric constant of the material used.

The principal advantage of this arrangement lies in the simple introduction of the sample and the improvement in the sensitivity of measurement owing to the double irradiation by the reflection of the microwave at the short-circuited end of the measurement cell. Although frequency modulation is conventional in resonator measuring technology, single reflection measurement cells had hitherto been avoided in measuring arrangements. However, it has been found that effects of parasitic resonances, for example in the case of coarse granulates, may be averaged out in this way with slightly different positioning of the individual grains, thus allowing for a reproducible formation of the measured value. The short-circuited end section of a circular cross-section tubular conductor may advantageously be used as the measurement cell by exciting the $H_{11}$ or $H_{01}$ mode. The wide-band and low-reflection coupling of the measurement cell is carried out in this case via a polytetrafluoraethylene (PTFE) cone which completely fills the transition to the flanged-on rectangular cross-section tubular conductor with $H_{10}$ mode radiation.

In a further development, the short circuit plate also functions as a detachable lid for the sample container and it is provided with a $\lambda/2$ short-circuit section projecting into the sample container. This short circuit section forms a reproducible microwave contact, free of metallic contacts, with the tubular conductor. The lid is advantageously joined to the sample container by means of a bayonet or snap fastener allowing for reproducible positioning in rotation and displacement with respect to the sample container.

The sample container is advantageously guided in the cylindrical tubular conductor by means of guide rings and consists of PTFE or a similar low-loss material having a low water-absorbing capacity. In the inserted position, the sample container lies without an air gap on the base of a PTFE cone. The sample container is slid without gaps in the cylindrical tube by means of the guide rings. The sample container may thus be introduced and removed easily. It is very important for the sample container to be able to be placed directly on scales so as to weigh in the desired amount product. This provides for rapid operation and thus reduces the risk of possible absorption of moisture from the ambient air, which is significant with hygroscopic substances. The reproducible functioning of the short-circuit plate is important for a high degree of accuracy in measurement. Sliding contacts and irradiation into the room are avoided by means described herein. As far as can be determined reflection is independent of rotation of the short-circuit plate.

The adaptation of the sample may be further improved if the sample container bears on its base a hollow PTFE cone which is also filled with the product and if the length of the hollow cone is greater than half of the length of the tube wave in the sample of powder. The adaptation must guarantee low-reflection coupling in and out of the radiation in the frequency range covered even when the dielectric data of the sample varies owing to changing composition and changing water content.

In the case of the materials with a higher moisture content or in the case of materials of higher density a simplified measurement cell may be used. A rectangular tube providing conduction of the $H_{10}$ mode is used instead of a circular tube. A cylindrical sample container composed of PTFE or quartz glass may be inserted from the short-circuited end in the axial direction so that the sample extends from the short-circuit plane into the rectangular waveguide. The sample container only partially fills the rectangular waveguide in this case and is located in the region of the maximum electric field. Recesses are provided in the centre of the wide sides of the rectangular waveguide and they also contribute to the homogenisation of the measured field.

In order to provide low-reflection coupling in and out of the microwave radiation, the cylindrical sample container may be sealed on the filling side with a double cone stopper composed of PTFE, the conical regions being at least a quarter of a tubular wavelength long. PTFE stoppers of different lengths are used for compensating the different bulk volumes of weighed out quantities of sample. This ensures that the product column is enclosed without air gaps.

A metal tube is used for introducing the sample container into the short-circuited rectangular waveguide and the cut-off wavelength of this metal tube is substantially smaller than the operating wavelength of the reflection measurement cell. This prevents microwave radiation from being emitted through the metal tube.

The rectangular tube measurement cell also affords the same advantages as the circular $H_{11}$ mode measurement cell, i.e. an increase in the sensitivity of measurement owing to the double irradiation of the sample, simple handling of the sample container, simple adaptation of the volume of sample to the range of moisture measurement and a high degree of accuracy in measurement owing to good field homogeneity in the travelling wave.

The microwave generator for the transmission arrangement is preferably a microwave oscillator whose frequency lies in the range of between 2 and 30 GHz, whose frequency deviation lies between 10 and 1000 MHz and whose modulation frequency lies between 1 Hz and 100 kHz. A circulator or a bidirectional waveguide coupler is connected upstream of the single reflection measurement cell to effect separation of the transmission signal.

The transmission signal and thus the microwave absorption produced by the product is advantageously measured by a difference circuit which forms the difference between the rectified microwave signal at the input of the measurement cell (reference signal) and the rectified microwave signal at the output of the measurement cell (transmission signal) and displays the result digitally. Thermoelectric voltages may be eliminated and the effect of variations in the oscillator output on the reading may be reduced in this way.

Embodiments of the invention are described in more detail below with reference to the accompanying drawings, in which:

FIG. 3 shows a single reflection measurement cell with a waveguide of rectangular cross-section and a sample inlet at the short circuit; and FIG. 4 shows a section along line A–B in FIG. 3;

FIG. 5 shows a section along line C–D in FIG. 3;

Figures 1, 2:
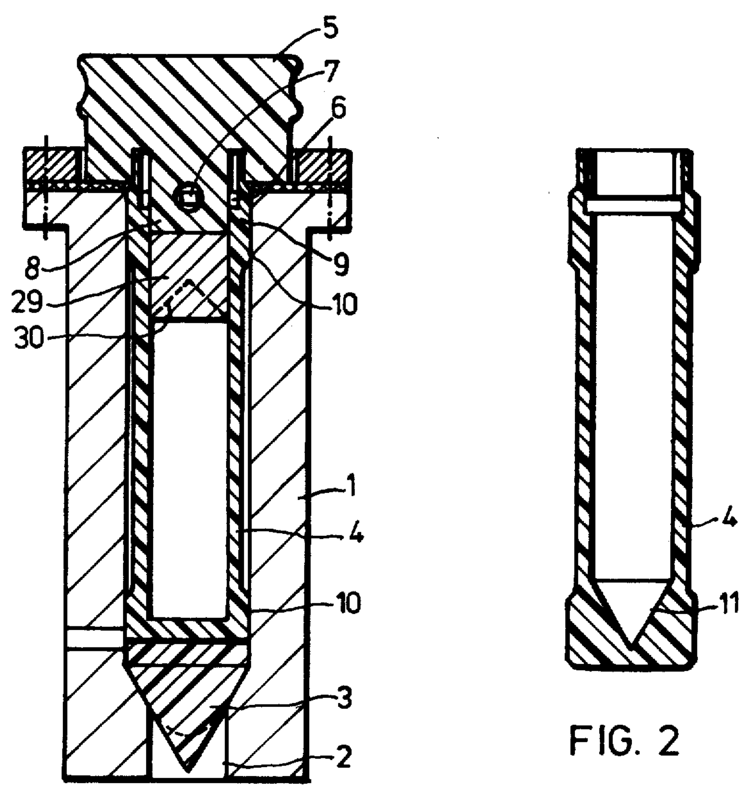
FIG. 1 shows a single reflection measurement cell with tubular conductor of circular cross-section.
FIG. 2 shows a sample container with a conical base.

The measurement cell in FIG. 1 consists of a cylindrical tube 1 in which the $H_{11}$ mode is excited. The tube 1 forms the end section of a rectangular waveguide 2 in which the $H_{10}$ mode is excited. The measurement cell is made non-reflective by use of a PTFE cone 3. A sample container 4 composed of PTFE may be placed from above in the cylindrical tube 1. The measurement cell is closed by a lid 5 provided with a bayonet fitting. The bayonet fitting has grooves 6 and the lid 5 has associated cams 7. A section 8 of the lid is formed as $\lambda/2$ short-circuit line. In the closed position, this part projects a distance $\lambda/2$ into the sample container 4. The gap 9 between the $\lambda/2$ section 8 and the inner wall of the tube 1 is considered as a $\lambda/2$ short-circuit groove. In this way, the lid 5 together with the section 8 forms, in the closed position, a contact-free microwave-tight and reproducible short circuit in the cylindrical tube 1. The bayonet cams 7 are produced from plastic so as to prevent parasitic resonances from being excited in the short-circuit groove 9.

The size of the sample container 4 is such that the sample of powder charged therein fills the internal diameter of the tube 1 practically completely. In particular, the length of the container is such that the container 4 rests exactly on the PTFE cone 3. The circumference of the sample container 4 is provided with guide rings 10 to enable it to slide smoothly in the measurement cell. The sample container may thus be easily introduced and removed so that the position in the measurement cell is always reproducible.

Instead of the non-rotationally-symmetrical $H_{11}$ mode which could cause dependence on the angle of rotation, the rotationally-symmetrical $H_{01}$ mode might be used but this could easily give rise to degeneration (simultaneous occurrence of various types of wave).

FIG. 2 shows a modified sample container 4 which does not have a planar seal at the lower end as in FIG. 1 but has a hollow cone 11. When the container is full, the powdery material forms a conical junction with the PTFE cone 3. Adaptation is thus improved as compared to the embodiment in FIG. 1. The two adaptation cones, the PTFE cone 3 and the hollow cone 11 filled with powdery sample, must ensure low reflection coupling in and out of the radiation in the frequency range covered, even when the dielectric data of the sample varies owing to the changes in chemical composition and in water content.

Frequency-modulated radiation (for example, a carrier of 9 GHz modulated with a frequency modulation of 400 MHz) is fed to the measurement cell so as to average out effects of parasitic resonances which may be produced, for example, in the case of coarse granulates, by markedly differing orientations of the individual grains. The range of moisture measurement may be determined by the total volume of the sample container 4 and by selection of the measurement frequency. In the case of a granulate with a moisture content of from 0.1 to 1% by weight and an average grain size of 1.5 mm, the sample container 4 has, for example, a length of 90 mm and a diameter of 30 mm. The measurement frequency is $9.2\pm0.2$ GHz in this case. The diameter of the reflection measurement cell is to be adapted to the value of the real component of the dielectric constant of the product so as to ensure high stability of the excited mode. Materials with a high dielectric constant thus require measurement cells of small internal diameter and vice versa. For example, cell diameters of 30 mm may be used for measuring the residual moisture of crimped fibres and plastic granulates at a measurement frequency of 9 GHz. When using the $H_{11}$ mode (known in English terminology as the $TE_{11}$ mode) in a circular waveguide, the diameter should lie in the range $0.6>\sqrt{\epsilon}D/\lambda>1.0$.

For materials with average or higher moisture or density, a measurement cell of the type shown in FIGS. 3 to 5 and 6 is preferably used. In this case, the sample container 4 is again located in the short-circuited end section of a tubular conductor. However, a rectangular tube conductor in which the $H_{10}$ (English $TE_{10}$) mode may be used instead of the round tube conductor in FIG. 1.

The cylindrical sample container 4 composed of quartz or PTFE only partially fills the rectangular tubular conductor 12. In this way, the sample container is substantially located in the homogeneous region of the E field. The short-circuit plane at the upper end of the measurement cell is designated by 13. In contrast to the embodiment of FIG. 1 the short-circuit plane is fixed in this case, i.e. it is also present when the lid 5 is removed. The sample container 4 is introduced into the measurement cell through a narrow cylindrical opening 14 in a neck-shaped section 15 at the upper end of the measurement cell. The diameter of the opening 14 coincides approximately with the external diameter of the sample container 4 and has to be sufficiently small to prevent microwave radiation from being emitted.

This is the case if the diameter d is smaller than the cut-off wavelength at the respective measurement frequency. For this purpose, d should be less than $\lambda/2\sqrt{\epsilon}$, where $\lambda$ is the wavelength and $\epsilon$ is the dielectric constant of a PTFE spacer 29. FIG. 4 shows a section along line A–B through the neck-shaped cylindrical section 15 of the tube 13.

The sample container 4 is provided with a double cone stopper 17 composed of PTFE for low-reflection coupling in and out of the microwave radiation.

In order to compensate for different bulk volumes of weighed out quantities of sample, PTFE stoppers of different lengths are used. This ensures that the product column is free of air gaps up to the conical intermediate part 30. The sample container is held in a reproducible and stable position in the rectangular waveguide by lateral recesses 18 in the wide side of the wave-guide (see FIG. 5). The recesses 18 also produce homogenisation of the measured field in the region of that part of the cross-section of the rectangular tube which is filled with product.

In order to achieve maximum accuracy of measurement, the diameter d and the length l of the volume of sample 4 are selected to be such that the typical microwave absorption of the product lies between 30 and 70%. The rectangular tube cross-section may be extended maximally to a square cross-section for receiving sample containers of larger diameter. These are preferably used with products of lower density.

The super-position of a wave travelling forwards and a wave travelling backwards gives rise to undesirable inhomogeneity of the measured field (the electric field strength depends on locality), which may be eliminated by two structural measures.

Figure 6:
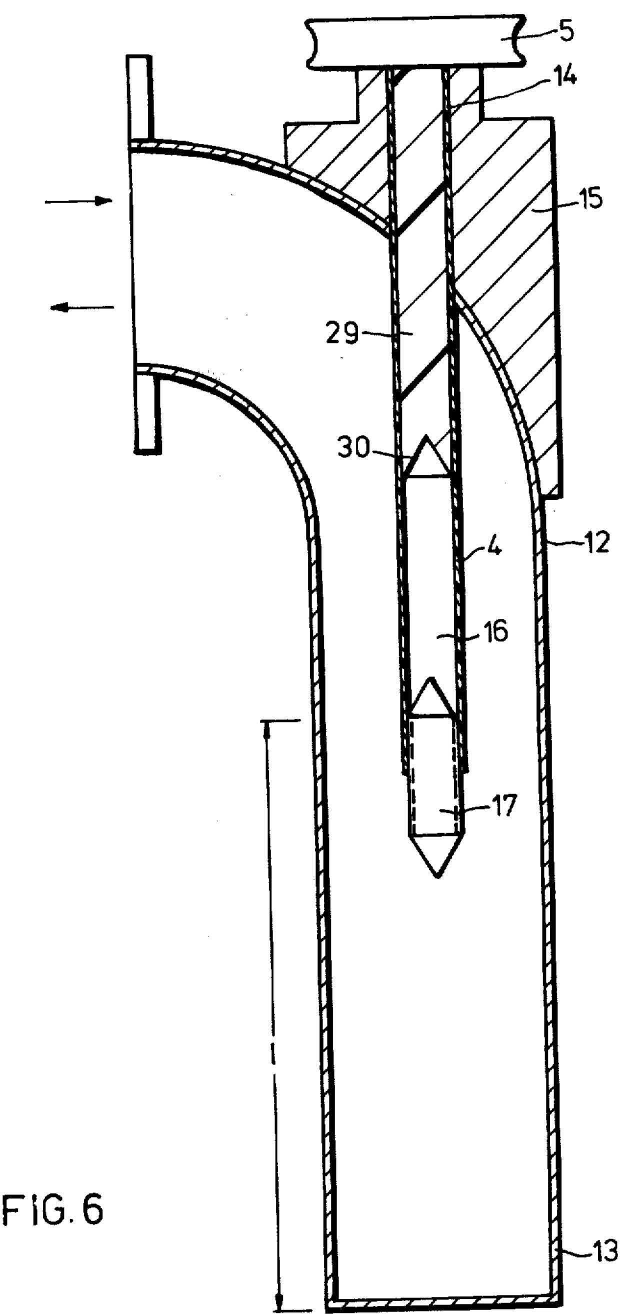
FIG. 6 shows a single reflection measurement cell with waveguide of rectangular cross-section and a sample inlet within a pipe bend.

The E field maximum is periodically displaced in relation to the reflection or short circuit plane 13 by using frequency-modulated microwave radiation with a frequency $f+\Delta f/2$ with a frequency deviation $\Delta f$ corresponding to $\Delta\lambda$. In order to homogenise the time average of the measured field completely, at the test position, a frequency deviation is used which is sufficient to induce a displacement of the maxima by $\pm$a quarter of a wavelength. The absolute value of the change in the position of the field maxima by the frequency modulation increases in proportion to the distance from the short-circuit plane. At the distance $n\lambda$ from the short-circuit plane, the displacement is $n\Delta\lambda$, where the frequency-modulated radiation is characterised by $\lambda\pm\Delta\lambda$. If the sample is at a distance $n\lambda$ from the short-circuit plane, then a minimum frequency deviation $\Delta\lambda$ corresponding to $n\Delta\lambda=\lambda/4$ i.e. $\Delta\lambda=\lambda/4n$ is required to displace the E field maximum by at least $\lambda/4$. For example, if n=5, then a deviation of $\lambda/20$ at 9 GHz of 450 MHz is necessary. The tighter the sample lies on the short-circuit plane, i.e. the smaller n becomes, the higher the minimum frequency deviation required for homogenising the measured field. Since normal commercial microwave generators only allow a limited deviation, the minimum distance between the sample and the short-circuit plane 13 is determined by filling the tubular conductor or the sample container upstream of the short-circuit plane with a loss-free dielectric, for example polytetrafluoroethylene or as shown in FIG. 6, a correspondingly large distance is provided between the sample 16 and the short circuit end 13 of the tubular conductor. The electrical length of this spacer 29 (FIG. 3) only needs to be $(n/2)\lambda$ since the interfering waves traverse this spacer twice. The geometric length l of the spacer is $l=n\lambda/2\sqrt{\epsilon}$, taking into consideration the real component of the dielectric constant $\epsilon'$ of the material used. In accordance with the example given above, for $n=5$ with PTFE 1 at 58 mm at doubled frequency deviation, the half value etc. is given. The transition from the dielectric to the volume of the sample 16 is formed by an intermediate part 30 of continuously tapering cross-section and of length $\lambda/4$ (cone or taper) in such a way that interfering reflections on the sample/dielectric interface are avoided. The same structural principles also apply to the embodiment of measurement cell shown in FIGS. 1 and 2.

Instead of the frequency-modulated radiation, monochromatic radiation may also be used if a loss-free phase modulator with a minimum deviation of 90° is used instead of the spacer.

The rectangular tube measurement cell also affords the same advantages as the $H_{11}$ mode measurement cell described above, namely an increase in the sensitivity of measurement owing to double irradiation of the sample, simple handling of the sample container, good possibilities for adaptation of the volume of sample to the desired range of moisture measurement and homogeneity made possible by measurement with travelling waves.

Figure 7:
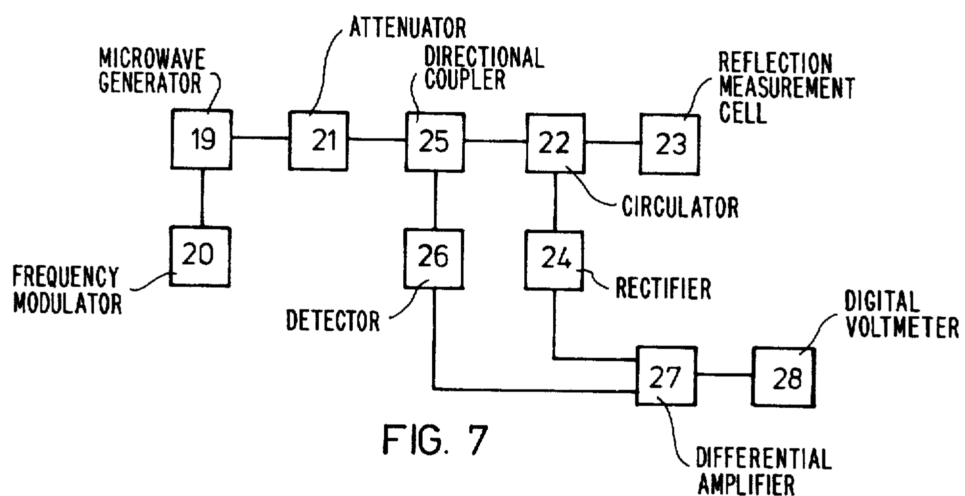
FIG. 7 is a block diagram for a microwave moisture-measuring instrument with a single reflection measurement cell.

FIG. 7 is a block diagram showing a measurement circuit for the reflection measurement cells described above. With this circuit, it is possible to measure relatively small to average volumes of sample of from 1 to 1000 $cm^3$ having a moisture content of between about 0.5 and 25% by weight in the frequency range of from 3 to 30 GHz with a reproducibility of ±0.5%. The microwave generator 19 is modulated in synchronism with the modulator 20 and feeds the reflection measurement cell 23 via an attenuator 21 and a circulator 22. After travelling forwards and backwards (transmission twice through the product) the returning signal is separated from the incoming microwave by the circulator 22 and is rectified with by a microwave rectifier 24. A reference signal is also branched off the incoming signal by a directional coupler 25 and is rectified by a microwave detector 26. The rectified signals are fed to a differential amplifier 27. The difference between the two direct voltages is displayed by a digital voltmeter 28. The frequency modulation of the microwave signal effected by the frequency modulator 20 serves both to homogeneise the field at the test position and to help to average out the interference caused by the varying values of the dielectric constant of the product from parasitic resonances on to the formation of the measured value.

Instead of the circulator 22 for separating a forward and backward travelling wave, a bi-directional waveguide coupler with reference and measurement detectors at its outputs may be used. However, an undesirable attenuation of the measurement signal (reflected wave) is produced in this case. In addition, a disadvantageous reaction of the microwave circuit may be produced on the oscillator. It has been found that accuracy of measurement is increased by using a circulator.

What we claim is:

1. An apparatus for measuring the water content of an electrically non-conductive isotropic material, comprising a microwave oscillator, means for frequency modulating the oscillator within the absorbing frequency range of the material, a closed, single-reflection, measurement cell supplied with microwaves from the oscillator, the measurement cell comprising a waveguide of one of circular and rectangular cross-section and a short-circuit plate terminating same such that two planar travelling waves with a homogeneous field distribution are present in the measurement cell during use, a sample container chargeable into the measurement cell and at least partially filling at least an end section thereof and means for measuring the microwave signal transmitted through the sample.

2. An apparatus according to claim 1, wherein the deviation of the frequency modulation is sufficiently large for the periodic displacement of the field strength maxima in the waveguide to be at least ±a quarter of a wavelength.

3. An apparatus according to claim 2, wherein one of the $TEM_{11}$ and $TEM_{01}$ mode is excited in the measurement cell, wherein the measurement cell comprises a circular cross-section tubular conductor, and a rectangular waveguide coupled in wide band and non-reflective fashion to the circular conductor and fed with radiation in the $TEM_{10}$ mode.

4. An apparatus according to claim 3, wherein the coupling comprises a transition completely filled with a cone of a low-loss material.

5. An apparatus according to claim 4, wherein the sample container comprises wide rings for precisely guiding the container in the cylindrical tubular conductor and is composed of a low-loss material having a low water-absorbing capacity, and, when inserted in the measurement cell, rests on the base of the said cone without an air gap.

6. An apparatus according to claim 5, wherein the low-loss material of the tube comprises one of polytetrafluoroethylene and quartz.

7. An apparatus according to claim 5, wherein the sample container comprises a base in the configuration of a hollow cone of low-loss material which is also fillable with the product, the length of the hollow cone being greater than half a wavelength of the microwaves in the sample.

8. An apparatus according to claim 7, wherein the low-loss material of at least one of the cones is polytetrafluoroethylene.

9. An apparatus according to claim 5 further comprising a lid and means for detachably connecting same to the sample container, wherein the lid comprises the short-circuit plate and has a short-circuit section $\lambda/2$ in length projecting into the sample container, the short-circuit section forming a microwave contact, free of any metallic contact, with the tubular conductor when the plate functions as the lid.

10. An apparatus according to claim 9, wherein means detachably connecting the lid comprises one of a bayonet and snap fastener for effecting the reproducible positioning of the lid with regard to rotation and displacement, with respect to the sample container.

11. An apparatus according to claim 2, wherein the measurement cell comprises a rectangular cross-section tube in which a $TEM_{10}$ mode wave is excitable and having a short-circuited end, and wherein the sample container is cylindrical and is composed of a low-loss material, a loss-free dielectric spacer in the cell having a conical end and a length l given by $l=(n/2)\cdot\lambda/\sqrt{\epsilon'}$, where $1 \leq n \leq 100$, $\lambda$ is the wavelength in the rectangular tube and $\epsilon'$ is the dielectric constant of the said dielectric in the rectangular tube and wherein the sample container is inserted axially into the tube from the short-circuited end until a column of sample in the container extends from the conical end and into the tube.

12. An apparatus according to claim 2 wherein the measurement cell is a rectangular cross-section tube having a pipe bend therein and in which a $TEM_{10}$ mode wave is excited and having a short-circuited end, and a cylindrical sample container composed of a low-loss material and including a closure member having a conical end and a spacer having a first cone on one end thereof and wherein the sample container is inserted in the region of the pipe bend until a column of sample in the container is located in the homogeneous electric field between the first cone and the conical end of a closure member, so that the distance from the lower end of the column of sample at the conical end to the short circuit plate of the rectangular tube is given by $l = n \cdot \lambda / 2\sqrt{\epsilon'}$, where $1 \leq n \leq 100$, $\lambda$ is the wave length in the rectangular tube, and $\epsilon'$ is the dielectric constant in the range l within the rectangular tube.

13. An apparatus according to claim 11, wherein the cylindrical sample container is arranged in the region of the maximum electric field, and recesses are provided in the centre of the wide sides of the rectangular tube for guiding the sample container.

14. An apparatus according to claim 13, further comprising means for effecting low-reflection coupling in and out of the micro-wave energy comprising a movable closure member of low-loss material having a conical region at each end, each of which is at least one quarter of a tube wavelength long, the closure member fixing the sample material in the container without an air gap.

15. An apparatus according to claim 14 further comprising means for introducing the sample container into the cell at the short-circuited end comprising a metal tube whose cut-off wavelength is substantially smaller than the operating wavelength of the reflection measurement cell.

16. An apparatus according to claim 1, wherein the frequency of the microwave oscillator lies in the range between 2 and 30 GHz, the frequency deviation between 10 and 1000 MHz, and the modulation of the frequency between 1 Hz and 100 kHz.

17. An apparatus according to claim 1, further comprising a circulator connected upstream of the measurement cell for separating off the transmission signal.

18. An apparatus according to claim 1, wherein the measuring means comprises a difference circuit which forms the difference between a rectified microwave signal at the input of the measurement cell and a rectified microwave signal at the output of the measurement cell.

19. An apparatus according to claim 1, further comprising means for digitally displaying the output of the measuring means.

20. An apparatus according to claim 1, further comprising means detachably connecting the short circuit plate to the sample container to provide a lid therefor and wherein the short circuit plate has a short circuit section $\lambda/2$ in length projecting into the sample container to simultaneously form a microwave contact free of any metallic contact with the waveguide.

* * * * *